United States Patent
Lee et al.

(10) Patent No.: US 11,206,969 B2
(45) Date of Patent: Dec. 28, 2021

(54) METHOD AND APPARATUS FOR TRACKING POSITION OF CAPSULE ENDOSCOPE

(71) Applicant: AJOU UNIVERSITY INDUSTRY-ACADEMIC COOPERATION FOUNDATION, Suwon-si (KR)

(72) Inventors: Jung Won Lee, Seoul (KR); Ye Seul Park, Incheon (KR); Gyu Bon Hwang, Yongin-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 455 days.

(21) Appl. No.: 16/108,248

(22) Filed: Aug. 22, 2018

(65) Prior Publication Data

US 2019/0125173 A1    May 2, 2019

(30) Foreign Application Priority Data

Oct. 26, 2017    (KR) .................. 10-2017-0140437

(51) Int. Cl.
*A61B 1/04*       (2006.01)
*A61B 1/00*       (2006.01)
(Continued)

(52) U.S. Cl.
CPC .......... *A61B 1/041* (2013.01); *A61B 1/00009* (2013.01); *A61B 1/00147* (2013.01);
(Continued)

(58) Field of Classification Search
CPC ... A61B 1/041; A61B 1/00158; A61B 5/6861; A61B 2562/162; A61B 5/0059;
(Continued)

(56) References Cited

U.S. PATENT DOCUMENTS

| | | | |
|---|---|---|---|
| 10,860,930 B2 * | 12/2020 | Shiratani | ............. G06K 9/6269 |
| 2003/0139661 A1 * | 7/2003 | Kimchy | ................ A61B 1/041 |
| | | | 600/407 |

(Continued)

FOREIGN PATENT DOCUMENTS

| | | | |
|---|---|---|---|
| JP | 2009-131319 A | 6/2009 | |
| JP | WO2017175282 A1 * | 2/2019 | ......... A61B 1/00009 |

OTHER PUBLICATIONS

Communication dated Mar. 8, 2019, issued by the Korean Patent Office in counterpart Korean Patent Application No. 10-2017-0140437.

*Primary Examiner* — Amanda Lauritzen Moher

(74) *Attorney, Agent, or Firm* — Sughrue Mion, PLLC

(57) ABSTRACT

Provided is a method for tracking a position of a capsule endoscope including: receiving, by an apparatus for tracking a position of a capsule endoscope, an image captured by the capsule endoscope; distinguishing, by the apparatus for tracking a position of a capsule endoscope, a gastrointestinal tract junction from the image using a machine-learned classification model based on the gastrointestinal tract junctions; and tracking, by the apparatus for tracking a position (Continued)

of a capsule endoscope, the position of the capsule endoscope based on the distinguished gastrointestinal tract junctions.

7 Claims, 7 Drawing Sheets

(51) Int. Cl.
 *G06K 9/00* (2006.01)
 *G06T 7/00* (2017.01)
 *G06N 20/00* (2019.01)
(52) U.S. Cl.
 CPC ......... *G06K 9/00496* (2013.01); *G06N 20/00* (2019.01); *G06T 7/0012* (2013.01)
(58) Field of Classification Search
 CPC ......... A61B 5/06; A61B 1/04; A61B 1/00045; A61B 1/00057; A61B 1/00; A61B 5/07; A61B 1/00009; A61B 1/00147; A61B 1/00059; G06T 2207/10068; G06T 2207/30028; G06T 7/70; G06T 7/0012; H04N 19/139; G06K 9/00496; G06N 20/00
 See application file for complete search history.

(56) References Cited

U.S. PATENT DOCUMENTS

| | | | |
|---|---|---|---|
| 2005/0148847 A1* | 7/2005 | Uchiyama | A61B 5/07 600/407 |
| 2008/0242926 A1 | 10/2008 | Nishino | |
| 2008/0242931 A1* | 10/2008 | Nishino | A61B 5/065 600/117 |
| 2009/0240108 A1* | 9/2009 | Shimizu | A61B 1/041 600/109 |
| 2010/0217079 A1* | 8/2010 | Tichy | A61B 34/70 600/118 |
| 2012/0316421 A1 | 12/2012 | Kumar et al. | |
| 2013/0237809 A1* | 9/2013 | Hasegawa | A61B 1/00016 600/424 |
| 2014/0303435 A1* | 10/2014 | Taniguchi | A61B 1/00045 600/103 |
| 2015/0138329 A1* | 5/2015 | Braun | A61B 1/00016 348/71 |
| 2016/0135668 A1* | 5/2016 | Gat | A61B 5/062 600/118 |
| 2016/0270639 A1* | 9/2016 | Trollsas | A61B 5/14539 |
| 2017/0004620 A1* | 1/2017 | Kitamura | A61B 1/00009 |
| 2018/0168490 A1* | 6/2018 | Jones | A61B 5/742 |

* cited by examiner

[FIG. 1]
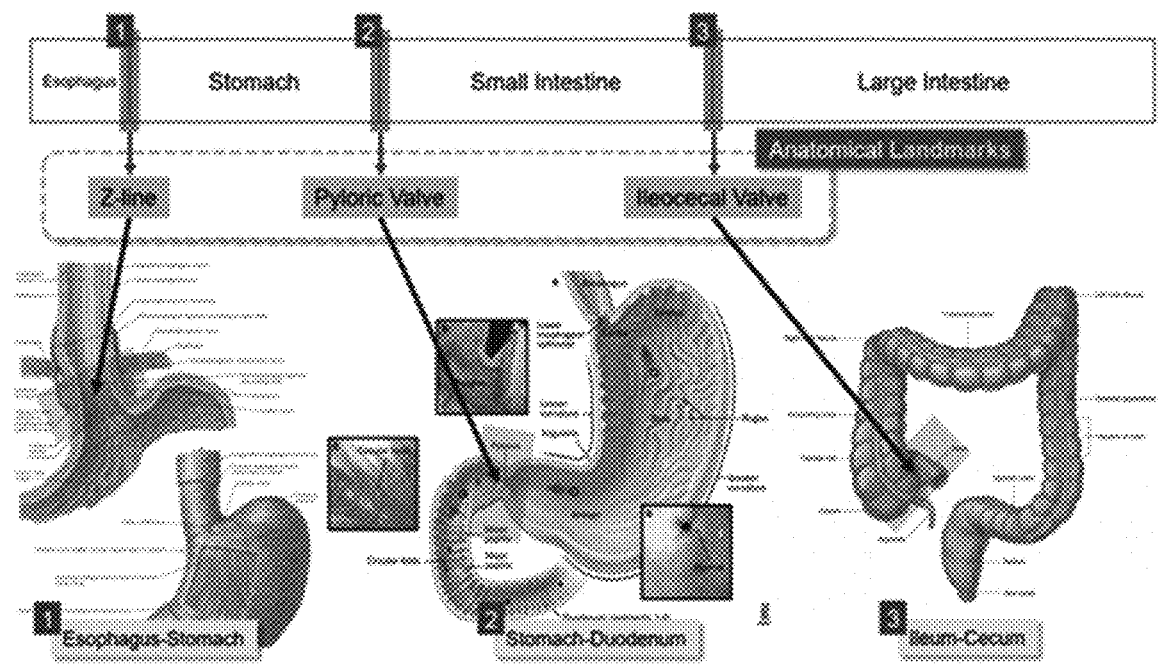

[FIG. 2]
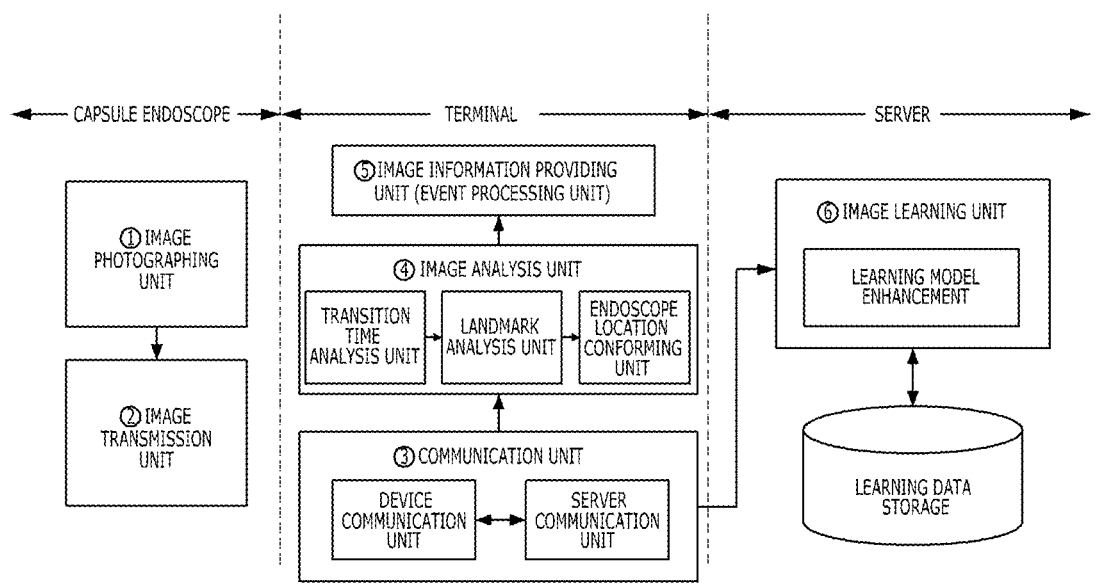

[FIG. 3]
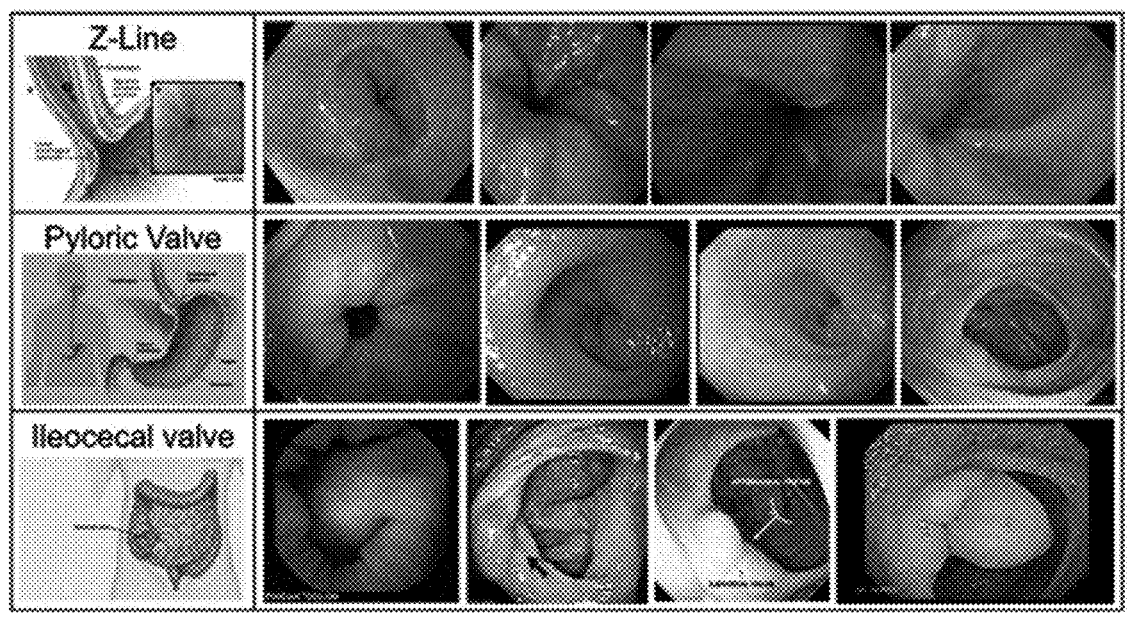

[FIG. 4]
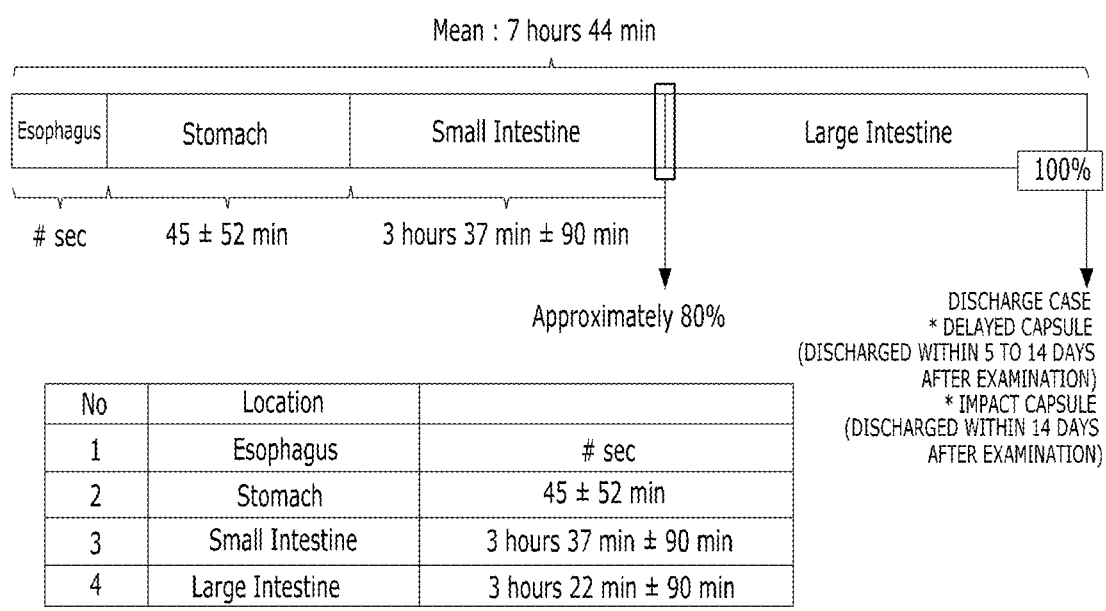

[FIG. 5A]

```
#define TransitionTime_ESOPHAGUS            300sec
#define TransitionTime_STOMACH_mean         45min
#define TransitionTime_STOMACH_var          52min
#define TransitionTime_SMALLINTESTINE_mean  217min
define TransitionTime_SMALLINTESTINE_var   307min Function checkGIValve (Image)
{
        if(Image is similar to Valve by using model (e.g.,: CNN model))
                return True;
            else
                return False;
}
```

[FIG. 5B]

```
Function checkTransitionTime (currentTransitionTime, currentGIPosition)
{
    switch(GI_position)
       case 'Esophagus':
           if(currentTransitionTime < TransitionTime_ESOPHAGUS)
                   return 'normal';
       case 'Stomach':
           if(currentTransitionTime < TransitionTime_STOMACH_mean)
                   return 'normal';
           else if(currentTransitionTime > TransitionTime_STOMACH_mean &&
                  currentTransitionTime < TransitionTime_STOMACH_var)
                   return 'normal';
           else
                   return 'abnormal';
```

[FIG. 5C]

```
Function checkTransitionTime (currentTransitionTime, currentGIPosition)
{
    switch(GI_position)
        case 'Small_Intestine':
            if(currentTransitionTime < TransitionTime_SMALLINTESTINE_mean)
                    return 'normal';
            else if(currentTransitionTime > TransitionTime_SMALLINTESTINE_mean &&
                    currentTransitionTime < TransitionTime_SMALLINTESTINE_var )
                    return 'normal';
            else
                    return 'abnormal';
}
```

[FIG. 5D]

```
Int main()
{
    if(checkGIValve)
    {
        currentTransitionTime = 0;                                    # reset
        currentGIpostition = currentGIposition->next;    # WHEN GI VALVE IS OBSERVED,
                                                         MOVE NEXT ORGAN if(checkTransitionTime(currentTransitionTime, currentGIPosition)='abnormal')
            RetentionAlarming;
    }
    else
    {
        if(checkTransitionTime(currentTransitionTime, currentGIPosition)='abnormal')
            RetentionAlarming;
    }
}
```

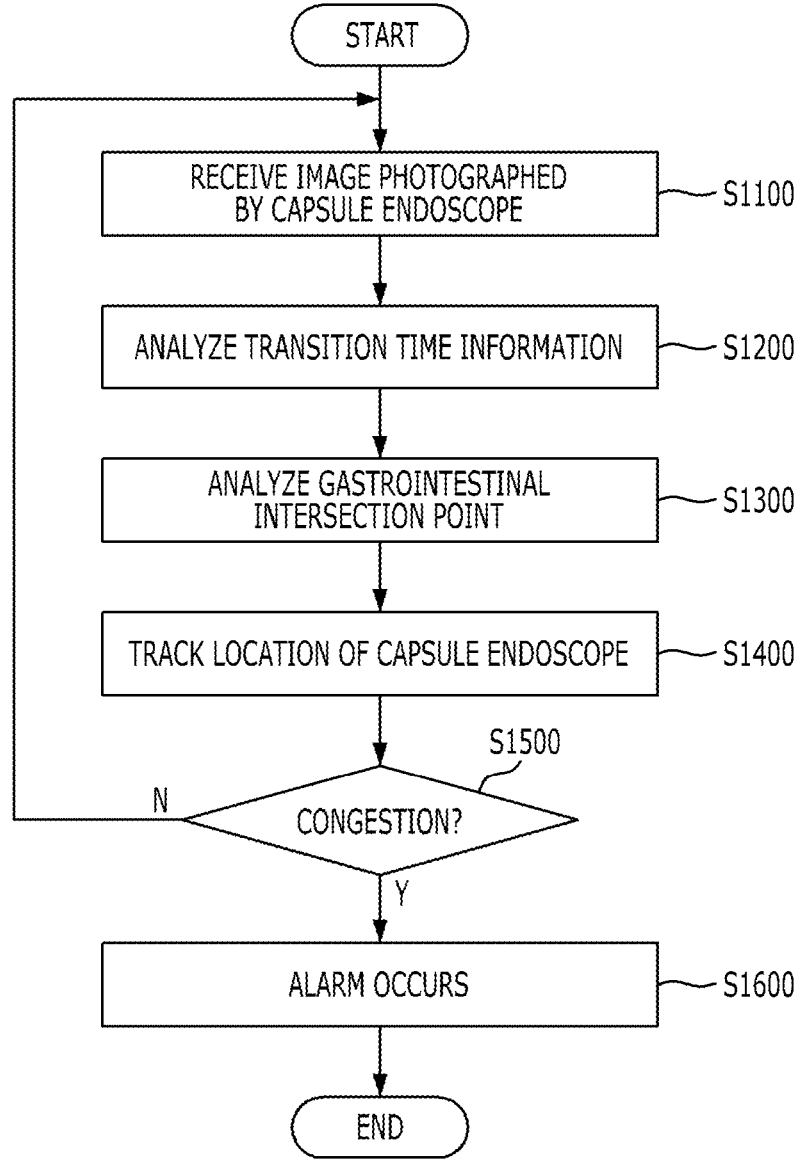
[FIG. 6]

METHOD AND APPARATUS FOR TRACKING POSITION OF CAPSULE ENDOSCOPE

CROSS-REFERENCE TO RELATED APPLICATIONS

This application claims the priority of Korean Patent Application No. 10-2017-0140437 filed on Oct. 26, 2017, in the Korean Intellectual Property Office, the disclosure of which is incorporated herein by reference.

BACKGROUND

Field

The present disclosure relates to a method and an apparatus for tracking a position of a capsule endoscope, and more particularly, to a method for tracking a position of a capsule endoscope through a machine learning and an apparatus for performing the method thereof.

Description of the Related Art

A capsule endoscope is an apparatus which is inserted into the human body to capture images in the body in order to observe a gastrointestinal tract. Unlike conventional endoscopy, the capsule endoscope is an endoscopic device that has an advantage of being able to be inserted into the human body without any foreign body sensation or discomfort to photograph the gastrointestinal tract. In addition, the capsule endoscope has a convenience of allowing a testee to freely move until being discharged after being inserted into the human body.

In general, for the analysis of images of the capsule endoscope, it is necessary to confirm the location (esophagus, stomach, jejunum, ileum, and the like) of the capsule and information (tumor, polyp, fungus, and the like) found at the location. However, due to the characteristics of digestive organs, when a capsule endoscopy is performed on a patient, images for about 14 to 18 hours are obtained, and thus, a large amount of time is consumed to analyze a large amount of images.

To this end, various studies are currently conducted to track the location of the capsule endoscope. For example, in KR 10-1055322 B1 entitled "endoscope and method for determining location of endoscope", in order to determine the position of the endoscope, an electrode is provided in an endoscope body to generate an electric signal in the endoscope body and determine a position of the endoscope through communication with a terminal device. Further, in KR 10-1405416 B1 entitled "endoscope system including position detecting function and method for detecting position of endoscope using the same", in order to determine the position of the endoscope, a value of an acceleration sensor installed in the endoscope is used. However, this conventional method has a difficulty in tracking the position in a lot of cases where positions are overlapped or not accurate.

In addition, in the case of the capsule endoscope, the capsule passes through the digestive tract by peristaltic movement, but the capsule endoscope does not pass through the digestive tract depending on the person and is retained in some organs. At present, this problem can not be solved because the position of the capsule is not tracked. In such a case, there is a problem in that a substantially and globally required image cannot be obtained even if photographing is performed over a long period of time. If a capsule retains in stomach, the images capturing small intestine or large intestine could not be obtained. Rather, in this case, it is necessary to help in identify a retention phenomenon to forcibly discharge the capsule endoscope.

There is a need for a method that can track the position of the capsule endoscope and provide an alarm when the retention phenomenon occurs.

SUMMARY

An object to be achieved by the present disclosure is to provide a method and an apparatus for tracking a position of a capsule endoscope.

The technical objects of the present disclosure are not restricted to the aforementioned technical objects, and other objects of the present disclosure which are not mentioned will become more apparent to one of ordinary skill in the art to which the present disclosure pertains by referencing the detailed description of the present disclosure given below.

According to an aspect of the present disclosure, there is provided a method for tracking a position of a capsule endoscope including: receiving, by an apparatus for tracking a position of a capsule endoscope, images captured by the capsule endoscope; distinguishing, by the apparatus for tracking a position of a capsule endoscope, gastrointestinal tract junctions from the images using a machine-learned classification model based on the gastrointestinal tract junctions; and tracking, by the apparatus for tracking a position of a capsule endoscope, the position of the capsule endoscope based on the distinguished gastrointestinal tract junctions.

Preferably, the method for tracking a position of a capsule endoscope may further include distinguishing, by the apparatus for tracking a position of a capsule endoscope, a transition time from the image; and determining, by the apparatus for tracking a position of a capsule endoscope, the retention of the capsule endoscope based on the transition time and the position of the capsule endoscope.

Preferably, the method for tracking a position of a capsule endoscope may further include providing, by the apparatus for tracking a position of a capsule endoscope, an alarm when it is determined that the capsule endoscope is retained.

Preferably, the determining of the retention of the capsule endoscope may include determining that the capsule endoscope is retained when the transition time exceeds a predetermined threshold time for each gastrointestinal tract based on the position of the capsule endoscope.

Preferably, the determining of the retention of the capsule endoscope may include personalizing the threshold time for each gastrointestinal tract based on at least one of gender, age, height, and weight of a testee using the capsule endoscope.

Preferably, the tracking of the position of the capsule endoscope may include determining the position of the capsule endoscope as the esophagus before a Z-line which is the first gastrointestinal tract junction is distinguished from the captured image.

Preferably, the tracking of the position of the capsule endoscope may include determining the position of the capsule endoscope as the stomach before a pyloric valve which is a second gastrointestinal tract junction is distinguished after the Z-line which is the first gastrointestinal tract junction is distinguished from the captured image.

Preferably, the tracking of the position of the capsule endoscope may include determining the position of the capsule endoscope as the small intestine (especially ileum which is last part of small intestine) before a ileocecal valve which is a third gastrointestinal tract junction is distinguished after the pyloric valve which is the second gastrointestinal tract junction is distinguished from the captured image.

Preferably, the tracking of the position of the capsule endoscope may include determining the position of the capsule endoscope as the large intestine (especially ascending colon which is initial part of large intestine) after a ileocecal valve which is the third gastrointestinal tract junction is distinguished from the captured image.

According to another aspect of the present disclosure, there is provided an apparatus for tracking a position of a capsule endoscope including: a communication unit configured to receive images captured by a capsule endoscope; an image analyzing unit configured to distinguish a gastrointestinal tract junction from the images using a machine-learned classification model based on the gastrointestinal tract junctions and track the position of the capsule endoscope based on the distinguished gastrointestinal tract junction; and an image information providing unit configured to determine retention of the capsule endoscope based on the transition time distinguished from the position of capsule endoscope and provide an alarm when it is determined that the capsule endoscope is retained.

According to yet another aspect of the present disclosure, there is provided a system for tracking a position of a capsule endoscope including: an apparatus for tracking a position of a capsule endoscope configured to distinguish a gastrointestinal tract junction from an image captured by a capsule endoscope using a machine-learned classification model based on the gastrointestinal tract junction and track the position of the capsule endoscope based on the distinguished gastrointestinal tract junction and track a position of the capsule endoscope based on the distinguished gastrointestinal tract junction; and a server configured to receive the image captured by the capsule endoscope from the apparatus for tracking the position of the capsule endoscope and generate a classification model of gastrointestinal tract junction by various machine-learning algorithms.

The effects according to the present disclosure are as follows.

In the present disclosure, it is possible to track an observing portion (anatomical landmark: esophagus, stomach, small intestine, and large intestine) of the capsule through the learning of the gastrointestinal tract junction images (a Z-line, a pyloric valve, and an ileocecal valve), which is a point where the gastrointestinal tract can be partitioned. This is a method of partitioning and analyzing the entire gastrointestinal tract, which may be observed in a capsule endoscope, into gastrointestinal tract junctions, it is possible to enable a rough position of the capsule to be tracked and solve a capsule retention problem by performing an event alarming process when the capsule is left in one organ for a long time.

The effects of the present disclosure are not limited to the aforementioned effects, and other objects, which are not mentioned above, will be more apparently understood to one of ordinary skill in the art from the following disclosure.

BRIEF DESCRIPTION OF THE DRAWINGS

The above and other aspects, features and other advantages of the present disclosure will be more clearly understood from the following detailed description taken in conjunction with the accompanying drawings, in which:

FIG. 1 is a diagram for describing a gastrointestinal tract junction which may be used in an exemplary embodiment of the present disclosure;

FIGS. 2 to 3 are diagrams for describing apparatus for tracking a position of a capsule endoscope according to an exemplary embodiment of the present disclosure;

FIG. 4 is a diagram for describing a process of determining whether or not to be congested which may be used in an exemplary embodiment of the present disclosure;

FIGS. 5A to 5D are diagrams for describing an algorithm for determining whether or not to be congested which may be used in an exemplary embodiment of the present disclosure; and FIG. 6 is a flowchart of a method for tracking a position of a capsule endoscope according to an exemplary embodiment of the present disclosure.

DETAILED DESCRIPTION OF THE PREFERRED EMBODIMENT

The present disclosure may have various modifications and various exemplary embodiments and specific exemplary embodiments will be described in detail. However, this does not limit the present disclosure to specific exemplary embodiments, and it should be understood that the present disclosure covers all the modifications, equivalents and replacements included within the idea and technical scope of the present disclosure. Like reference numerals generally denote like elements when describing each drawing.

Terms, such as first, second, A and B may be used to describe various components and the components should not be limited by the terms. The terms are used to only distinguish one constituent element from another component. For example, a first component may be referred to as a second component, and similarly, the second component may be referred to as the first component without departing from the scope of the present disclosure. A term 'and/or' includes a combination of a plurality of associated disclosed items or any item of the plurality of associated disclosed items.

It should be understood that, when it is described that a component is "connected to" or "accesses" another component, the component may be directly connected to or access the other component or a third component may be present therebetween. In contrast, it should be understood that, when it is described that an element is "directly connected to" or "directly access" another element, it is understood that no element is present between the element and another element.

Terms used in the present application are used only to describe specific embodiments, and are not intended to limit the present disclosure. Singular expressions used herein include plural expressions unless they have definitely opposite meanings in the context. In the present application, it should be understood that term "include" or "have" indicates that a feature, a number, a step, an operation, a component, apart or the combination thereof described in the specification is present, but does not exclude a possibility of presence or addition of one or more other features, numbers, steps, operations, components, parts or combinations thereof, in advance.

If it is not contrarily defined, all terms used herein including technological or scientific terms have the same meanings as those generally understood by a person with ordinary skill in the art. Terms defined in generally used dictionary shall be construed that they have meanings matching those in the context of a related art, and shall not be construed in ideal or excessively formal meanings unless they are clearly defined in the present application.

Hereinafter, preferred exemplary embodiments of the present disclosure will be described in detail with reference to the accompanying drawings.

FIG. 1 is a diagram for describing a gastrointestinal tract junction which may be used in an exemplary embodiment of the present disclosure.

Referring to FIG. 1, three gastrointestinal tract junctions are illustrated at an upper end. A first gastrointestinal tract junction is a junction between the esophagus and the stomach, which is called a Z-line. A second gastrointestinal tract junction is a junction between the stomach and the small intestine, which is called a pyloric valve. A third gastrointestinal tract junction is a point called an ileocecal valve.

In a method for tracking a capsule endoscope position based on a conventional algorithm of image processing, the esophagus or the stomach has clear characteristics, so that it is possible to accurately track the positions thereof, but there is a disadvantage that the small intestine or the large intestine is difficult to track the accurate position because similar images are continuously repeated. In addition, the method of tracking the position of the capsule endoscope due to the intensity of an electric signal has a limitation in that the positions tracked by the interference or refraction of the signal are overlapped or not accurate.

In order to overcome such disadvantages, the present disclosure proposes a method of determining the position of a capsule endoscope based on whether or not to pass through a gastrointestinal tract junction based on machine learning. Of course, even if the method proposed in the present disclosure is used, it is difficult to determine the exact position of the capsule endoscope, but it is possible to determine whether the capsule endoscope pass through at least any anatomical landmark (such as esophagus, stomach, small intestine and large intestine) in gastrointestinal tract in real time.

That is, the method may determine whether the capsule endoscope is positioned at the esophagus, the stomach, the small intestine or the large intestine according to whether there is the first gastrointestinal tract junction, whether there is the second gastrointestinal tract junction, or whether there is the third gastrointestinal tract junction from the image photographed by the capsule endoscope. Since the gastrointestinal tract junction is a partitioning point where one gastrointestinal tract is terminated and other tract is started, a hole that seems to be sucked in is observed. This can be a feature of the images and it makes it easy to learn the images.

Generally, the capsule endoscope has a major intention of photographing the small intestine and the large intestine. The reason is that the gastrointestinal tract such as the esophagus or the stomach can be photographed by a general endoscope rather that the capsule endoscope. However, the capsule endoscope has a limited battery due to its size limitation. When such a capsule endoscope is retained in a stomach for a long period of time, the limited battery is fully consumed and the image of the small intestine or the large intestine to be targeted is often not photographed.

This is because the capsule endoscope is merely moved by passive power. That is, the capsule endoscope merely moves through the peristalsis of the gastrointestinal tract without a separate power, so the time to pass through each part of gastrointestinal tract may be different in some cases. Of course, there is a certain tendency, but when the retention occurs, if this is not solved, there is a problem in the satisfaction of the testee.

That is, when the capsule endoscope is used, the testee can freely move to some extent, but the testee needs to carry a device for receiving the image and the like. As a result, when a desired image of the small intestine or the large intestine is not obtained after a long-term test is finished through the capsule endoscope, complaints of the testee about the capsule endoscope test may occur. Therefore, if the capsule endoscope is retained in a specific gastrointestinal tract for a long period of time, it is possible to alleviate the dissatisfaction of the testee when such a situation is guided to the testee.

In the method proposed in the present disclosure, the approximate position of the capsule endoscope is tracked, and as a result, when the capsule endoscope is retained in the specific gastrointestinal tract for a long time, an alarm may be provided to the testee and a tester. For example, when the capsule endoscope is retained in the stomach for a long time, the tester takes measures to the testee to help in forcedly discharging the capsule endoscope.

FIGS. 2 to 3 are diagrams for describing apparatus for tracking a position of a capsule endoscope according to an exemplary embodiment of the present disclosure.

The apparatus for tracking the position of the capsule endoscope according to the exemplary embodiment of the present disclosure may include a communication unit, an image analysis unit, and an image information providing unit. The communication unit receives the image captured by the capsule endoscope in real time through communication with the image transmitting unit of the capsule endoscope. For this purpose, a capsule endoscope includes an image capturing unit and an image transmitting unit.

Conventional capsule endoscopes are mainly based on transmission of images captured through communication in real time, rather than having separate storage spaces due to the limitation of the volume. To this end, after the testee swallows the capsule endoscope, a separate device is put on the shoulder in the form of a bag or in contact with the waist in the form of a belt. Then, the capsule endoscope receives and stores the captured images in real time through short-range communication.

In such a conventional method, a terminal just serves to receive and store the images of the capsule endoscope. However, in the method proposed in the present disclosure, a terminal not only receives and stores images of the capsule endoscope but also analyze the image captured by the capsule endoscope to determine whether the capsule endoscope passes through each gastrointestinal tract junction and whether the capsule endoscope is retained and provide an alarm.

The apparatus for tracking the position of the capsule endoscope proposed in the present disclosure is the apparatus illustrated as the terminal in FIG. 2, and for example, may be a device such as a smart phone. The apparatus for tracking the position of the capsule endoscope may receive the image captured by the capsule endoscope through a short distance communication such as Bluetooth, analyze the received image, and transmit the received image to a separate server through wireless communication.

To this end, the communication unit of the terminal may include a device communication unit and a server communication unit. The device communication unit is a communication module such as Bluetooth low energy (BLE) for short-range communication with the capsule endoscope. The server communication unit is a communication module such as 3G or long term evolution (LTE) for transmitting the image received from the capsule endoscope to a separate external server.

In the communication unit of the terminal, the device communication unit transmits and receives the image of the capsule endoscope with the image transmission unit in real time, or the server communication unit may transmit the received image in real time or transmit the received image in a predetermined period or aperiodically. The images transmitted to the server are used for machine learning to track the position of the capsule endoscope based on the gastrointestinal tract junction later.

The image analyzing unit of the terminal receives and mounts a classifier of the machine-learned gastrointestinal tract junction from the server. The classifier of the gastrointestinal tract junction is used to analyzing the received image in real time in the capsule endoscope in a classification model generated by the machine learning in advance. The image analyzing unit checks the position of the gastrointestinal tract junction from the image of the capsule endoscope by using the mounted classifier model and checks the approximate position of the capsule based thereon.

Referring to FIG. 2, the image analyzing unit of the apparatus for tracking the position of the capsule endoscope proposed in the present disclosure may include a transition time analyzing unit, a landmark analyzing unit, and an endoscope position checking unit. The transition time analyzing unit extracts and analyzes the transition time from the meta data of the image transmitted by the capsule endoscope. The transition time is used to determine whether or not the capsule endoscope is retained by comparison of transition time in normal case.

The landmark analyzing unit applies the machine-learned classification model based on the gastrointestinal tract junction to determine whether the image captured the capsule endoscope corresponds to the gastrointestinal tract junction. That is, the landmark analyzing unit receives the image from the capsule endoscope in real time and determines whether each image corresponds to a first gastrointestinal tract junction, a second gastrointestinal tract junction, or a third gastrointestinal tract junction.

The endoscope position checking unit determines a time correlation position of the capsule endoscope based on the transition time of the transition time analyzing unit and the presence or absence of the gastrointestinal tract junction of the landmark analyzing unit. That is, the endoscope position checking unit determines a position while passing through the esophagus based on whether the capsule endoscope has passed through the first gastrointestinal tract junction, determines a position while passing through the stomach based on whether the capsule endoscope has passed through the second gastrointestinal tract junction, and determines a position while passing through the small intestine or the large intestine based on whether the capsule endoscope has passed through the third gastrointestinal tract junction.

As a result, as illustrated in a lower right end of FIG. 2, a specific frame is extracted as the gastrointestinal tract junction, and frames between gastrointestinal tract junctions show esophagus, the stomach, the small intestine (duodenum jejunum and ileum), and large intestine. After the position of the capsule endoscope is determined, the determined position is transmitted to the image information providing unit and an alarm may be generated if necessary. To this end, the retention needs to be determined based on the approximate position of the capsule endoscope and the transition time. The related contents will be described in more detail in FIG. 4 below.

The image information providing unit suspects the retention of the capsule when the approximate position is not continuously changed but left even if a predetermined time and processes an event (alarming) that may be notified to the patient, the nurse or the doctor. The alarming may be guided through auditory and visual effects at the terminal. For example, a guidance message such as "the capsule endoscope is being retained in the stomach for a long time" may be provided to the testee or the nurse. Alternatively, the guidance message may be provided through a display (not illustrated) of the terminal. Alternatively, the guidance message may be transmitted to a designated terminal of the doctor or the nurse.

The apparatus for tracking the position of the capsule endoscope proposed in the present disclosure uses the machine-learned classification model in advance in the server. The server may include an image learning unit and a database for storing learning data. In the database, various images received from a plurality of terminals in advance are stored, and only the image corresponding to the gastrointestinal tract junction among the images may be selected and used for machine learning.

The image learning unit performs generating and advancing the learning model capable of classifying the gastrointestinal tract junction. The gastrointestinal tract junction is a section where the digestive tract is suddenly narrowed by the sphincter when passing from the esophagus to the stomach or passing from the stomach to the duodenum and may be photographed as illustrated in FIG. 3. There are deep-learning methods for creating a learning model by collecting lots of gastrointestinal tract junction images as illustrated in FIG. 3, and as such, the learned classifier model is mounted on the terminal to classify the frame for the gastrointestinal tract junction. Although the images in FIG. 3 are expressed in black and white, they may be expressed in color as well.

To this end, the image for the gastrointestinal tract junction is constructed as the big data. Next, learning of gastrointestinal tract junction images is performed by applying deep neural network model (for example, convolutional neural network (CNN)), and classification of the gastrointestinal tract junction images is performed by applying the learning model. The learned classifier model is mounted on the terminal, and as a result, the frame for the gastrointestinal tract junction is extracted.

By using the method proposed in the present disclosure, the image of the gastrointestinal tract junction (Z-line, pyloric valve, and ileocecal valve), which is a main point for dividing the capsule endoscope image for each region is learned by applying the deep learning method based on the big data and the recognition is performed to determine the approximate position of the capsule endoscope, thereby solving the problem of retention of the capsule endoscope.

Currently, the reason for the failure of the capsule endoscope imaging test mainly corresponds to a case where the capsule is retained in the stomach or intestines so as not to be discharged. In such a case, the medical information that can be acquired by the capsule endoscope cannot determine the status of patient, and the economic and time loss is also great. The present disclosure can provide a solution to such a retention phenomenon, so that the convenience of the testee can be improved.

FIG. 4 is a diagram for describing a process of determining whether or not to be retained which may be used in an exemplary embodiment of the present disclosure.

Referring to FIG. 4, the time at which each gastrointestinal tract junction is detected is indicated. For example, the first gastrointestinal tract junction, which is the border between the esophagus and the stomach, needs to be detected within several seconds (#sec) and the second gastrointestinal tract junction, which is the border between the stomach and the small intestine, needs to be detected within 45 minutes to +/−52 minutes after detection of the first gastrointestinal tract junction. The third gastrointestinal tract junction, which is the border between the small intestine and the large intestine, needs to be detected within 3 hours and 37 minutes to +/−90 minutes after detection of the second gastrointestinal tract junction. The point at which the third gastrointestinal tract junction is detected is a point corresponding to 80% of the entire capsule endoscope image. In addition, the discharged time needs to be generally detected within 3 hours and 22 minutes to +/−90 minutes after the detection of the third gastrointestinal tract junction. If the capsule endoscope is discharged between 5 and 14 days after the test, it is delayed.

The detection time of each gastrointestinal tract junction illustrated in FIG. 4 is a value proposed based on a test data of 500 patients using the capsule endoscope, but a detailed change can be changed according to a later case. For example, data on capsule endoscope patients may be collected considering gender, age, height, weight, and the like, and the detection time may be further subdivided based on the big data analysis. Through this, it is possible to determine whether or not the capsule endoscope is retained by applying a personalized detection time to each user.

FIGS. 5A to 5D are diagrams for describing an algorithm for determining whether or not to be retained which may be used in an exemplary embodiment of the present disclosure.

Referring to FIGS. 5A to 5D, a pseudo code of an algorithm for determining the retention is illustrated. First, in FIG. 5A, the transition time required for detection of the gastrointestinal tract junction described in FIG. 4 is defined as a constant. In addition, a checkGIValve function receives the received image as a parameter, compares the received parameter with the learning model, and determines whether the received parameter and the learning model are similar to each other. As a result, the image corresponding to the gastrointestinal tract junction may be extracted from the frame of each image.

Next, referring to FIGS. 5B to 5C, the checkTransitionTime function is used as the data to receive the current transition time and the current position of the capsule endoscope as a parameter, and determine the retention by comparing the detection time and the transition time of each gastrointestinal tract junction according to the position of the capsule endoscope. That is, when 'normal' is output as a result of the function, it is determined as the normal, and when 'abnormal' is output, it is determined as the retention (one function is displayed as two images due to a spatial limitation of the image).

Next, referring to a main function of FIG. 5D, whenever the gastrointestinal tract junction is detected, a function for detecting the next gastrointestinal tract junction is called to determine the retention. In the main function, the checkGIValue function described in FIG. 5A above or the checkTransitionTime function described in FIGS. 5B and 5C are called.

Until now, a process of determining the retention and providing the alarm through FIG. 4 and FIGS. 5A to 5D has been described. This process is summarized in the flowchart as illustrated in FIG. 6 below.

FIG. 6 is a flowchart of a method for tracking a position of a capsule endoscope according to an exemplary embodiment of the present disclosure.

Referring to FIG. 6, first, an image captured by a capsule endoscope is received through a short-range communication and the like (S1100). Thereafter, a transition time is analyzed in the corresponding image (S1200). From when the capsule endoscope is inserted through the oral cavity of the testee, the capturing time of images are stored by metadata. As a result, the transition time indicating how much time has passed after the capsule endoscope is inserted may be obtained. Alternatively, the transition time is already calculated in the capsule endoscope and may be stored in the metadata.

Next, based on the learning model received from the server in advance, the received image is analyzed and frames capturing the points corresponding each gastrointestinal tract junction are extracted (S1300). The approximate position of the capsule endoscope is tracked through this process (S1400). That is, the image is determined as the esophagus before passing through the first gastrointestinal tract junction, determined as the stomach before passing through the second gastrointestinal tract junction after passing through the first gastrointestinal tract junction, determined as the small intestine before passing through the third gastrointestinal tract junction after passing through the second gastrointestinal tract junction, and determined as the large intestine after passing through the third gastrointestinal tract junction.

Next, the transition time is compared with the position of the capsule endoscope to determine whether the capsule endoscope is retained (S1500). If the capsule endoscope is retained, the alarm of the retention is provided to the testee, the doctor, the nurse, and the like through the method set in advance. As a result, it is possible to solve the retention of the capsule endoscope. If the capsule endoscope is not retained, the images captured continuously by the capsule endoscope are received (S1100), and the above process is repeated.

Although embodiments of the present disclosure were described above with reference to the accompanying drawings, those skilled in the art would understand that the present disclosure may be implemented in various ways without changing the necessary features or the spirit of the prevent invention. Therefore, the embodiments described above are only examples and should not be construed as being limitative in all respects.

What is claimed is:

1. A method for tracking a position of a capsule endoscope, the method comprising:
    performing, by a communication unit included in an apparatus for tracking the position of the capsule endoscope, communication with the capsule endoscope from when the capsule endoscope is inserted through an oral cavity of a testee;
    receiving, by the communication unit, a current image captured by the capsule endoscope;
    obtaining, by an image analyzing unit included in the apparatus, a transition time from a metadata of the current image received by the communication unit;
    determining, by the image analyzing unit, whether the current image corresponds to a gastrointestinal tract junction of the testee by applying the current image to a classification model which is a model learned by using a machine-learning algorithm based on images for gastrointestinal tract junctions received from a plurality of terminals;
    determining, by the image analyzing unit, a position of the capsule endoscope based on the obtained transition time and whether the current image corresponds to the gastrointestinal tract junction;
    determining, by an image information providing unit included in the apparatus, a retention of the capsule endoscope based on the obtained transition time and the determined position of the capsule endoscope; and providing, by the image information providing unit, an alarm when it is determined that the capsule endoscope is retained,
wherein the determining of the retention of the capsule endoscope includes determining that the capsule endoscope is retained when the obtained transition time exceeds a predetermined threshold time for a gastrointestinal tract of the testee based on the determined position of the capsule endoscope, and
wherein the metadata stores a capturing time of the current image from when the capsule endoscope is inserted through the oral cavity of the testee.

2. The method for tracking the position of the capsule endoscope of claim 1, wherein the determining of the retention of the capsule endoscope includes personalizing the threshold time for the gastrointestinal tract of the testee based on one or more of gender, age, height, and weight of the testee using the capsule endoscope.

3. The method for tracking the position of the capsule endoscope of claim 1, where the gastrointestinal tract junction of the testee is one of a plurality of gastrointestinal tract junctions of the testee,
wherein the plurality of gastrointestinal tract junctions of the testee include a Z-line, a pyloric valve and an ileocecal valve, and
wherein the determining of the position of the capsule endoscope includes determining the position of the capsule endoscope as an esophagus of the testee before the Z-line is distinguished from the current image.

4. The method for tracking the position of the capsule endoscope of claim 1, where the gastrointestinal tract junction of the testee is one of a plurality of gastrointestinal tract junctions of the testee,
wherein the plurality of gastrointestinal tract junctions of the testee include a Z-line, a pyloric valve and an ileocecal valve, and
wherein the determining of the position of the capsule endoscope includes determining the position of the capsule endoscope as a stomach of the testee before the pyloric valve is distinguished from the current image and after the Z-line is distinguished from the current image.

5. The method for tracking the position of the capsule endoscope of claim 1, where the gastrointestinal tract junction of the testee is one of a plurality of gastrointestinal tract junctions of the testee,
wherein the plurality of gastrointestinal tract junctions of the testee include a Z-line, a pyloric valve and an ileocecal valve, and
wherein the determining of the position of the capsule endoscope includes determining the position of the capsule endoscope as a small intestine of the testee before the ileocecal valve is distinguished from the current image and after the pyloric valve is distinguished from the current image.

6. The method for tracking the position of the capsule endoscope of claim 1, where the gastrointestinal tract junction of the testee is one of a plurality of gastrointestinal tract junctions of the testee,
wherein the plurality of gastrointestinal tract junctions of the testee include a Z-line, a pyloric valve and an ileocecal valve, and
wherein the determining of the position of the capsule endoscope includes determining the position of the capsule endoscope as a large intestine of the testee after the ileocecal valve is distinguished from the current image.

7. An apparatus for tracking a position of a capsule endoscope, the apparatus comprising:
a communication unit configured to perform communication with the capsule endoscope from when the capsule endoscope is inserted through an oral cavity of a testee and receive a current image captured by the capsule endoscope;
an image analyzing unit configured to obtain a transition time from a metadata of the current image received by the communication unit, determine whether the current image corresponds to a gastrointestinal tract junction of the testee by applying the current image to a classification model which is a model learned by using a machine-learning algorithm based on images for gastrointestinal tract junctions received from a plurality of terminals, determine a position of the capsule endoscope based on the obtained transition time and whether the current image corresponds to the gastrointestinal tract junction of the testee; and
an image information providing unit configured to determine a retention of the capsule endoscope based on the obtained transition time and the determined position of the capsule endoscope and provide an alarm when it is determined that the capsule endoscope is retained,
wherein the image analyzing unit determines that the capsule endoscope is retained when the obtained transition time exceeds a predetermined threshold time for a gastrointestinal tract of the testee based on the determined position of the capsule endoscope, and
wherein the metadata stores a capturing time of the current image from when the capsule endoscope is inserted through the oral cavity of the testee.

\* \* \* \* \*